(12) United States Patent
Amely-Velez

(10) Patent No.: US 6,400,985 B1
(45) Date of Patent: Jun. 4, 2002

(54) METHOD AND APPARATUS FOR TIMING EVENTS WITHIN AN IMPLANTABLE MEDICAL DEVICE

(75) Inventor: Jorge N. Amely-Velez, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

(21) Appl. No.: 09/777,646

(22) Filed: Feb. 6, 2001

(51) Int. Cl.[7] .................................................. A61N 1/37
(52) U.S. Cl. ......................................................... 607/9
(58) Field of Search ...................................... 607/4–30

(56) References Cited

U.S. PATENT DOCUMENTS

| | | | |
|---|---|---|---|
| 4,390,022 A | 6/1983 | Calfee et al. | 128/419 |
| 4,624,260 A | 11/1986 | Baker, Jr. et al. | 128/419 |
| 4,625,730 A | 12/1986 | Fountain et al. | 128/419 |
| 4,712,555 A | 12/1987 | Thornander et al. | 128/419 |
| 4,788,980 A | 12/1988 | Mann et al. | 128/419 |
| 4,940,052 A | 7/1990 | Mann et al. | 128/419 |
| 4,944,298 A | 7/1990 | Sholder | 128/419 |
| 5,022,395 A | 6/1991 | Russie | 128/419 |
| 5,466,254 A | 11/1995 | Helland | 607/123 |
| 5,527,345 A | 6/1996 | Infinger | 607/4 |
| 5,545,182 A | 8/1996 | Stotts et al. | 607/5 |
| 5,554,174 A | 9/1996 | Causey, III | 607/5 |

FOREIGN PATENT DOCUMENTS

| | | | |
|---|---|---|---|
| EP | 0 550 344 A1 | 12/1992 | A61N/1/39 |
| FR | 0 549 438 A1 | 12/1992 | A61N/1/08 |
| RU | 878309 | 1/1980 | A61N/1/36 |

*Primary Examiner*—Scott M. Getzow

(57) ABSTRACT

A technique is described for timing hardware or software events for use in an implantable medical device capable of performing many concurrent processes. The technique exploits a first timer for timing events using a timing interval of one millisecond and a second timer or clock signal for timing events using a timing interval of two seconds. A receive unit receives timer requests from the many concurrent processes with each timer request specifying a time delay before an interrupt or other timer completion signal is required. A control unit uses either the first timer or the second timer to time the request based upon the time delay and the respective timing intervals. An interrupt or other timer completion signal is issued to the requesting device following the specified time delay as timed by the selected timer. For the purposes of prioritizing two or more timer requests to be timed by the same timer, the device also exploits the concept of a pseudo clock for tracking time up to a maximum pre-determined period of time of, for example, 65 seconds.

12 Claims, 8 Drawing Sheets

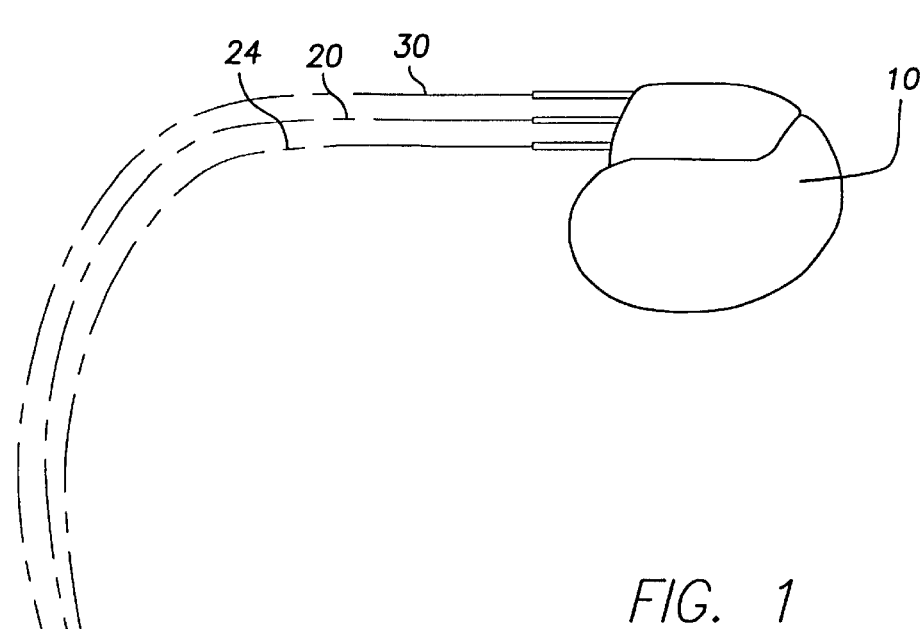
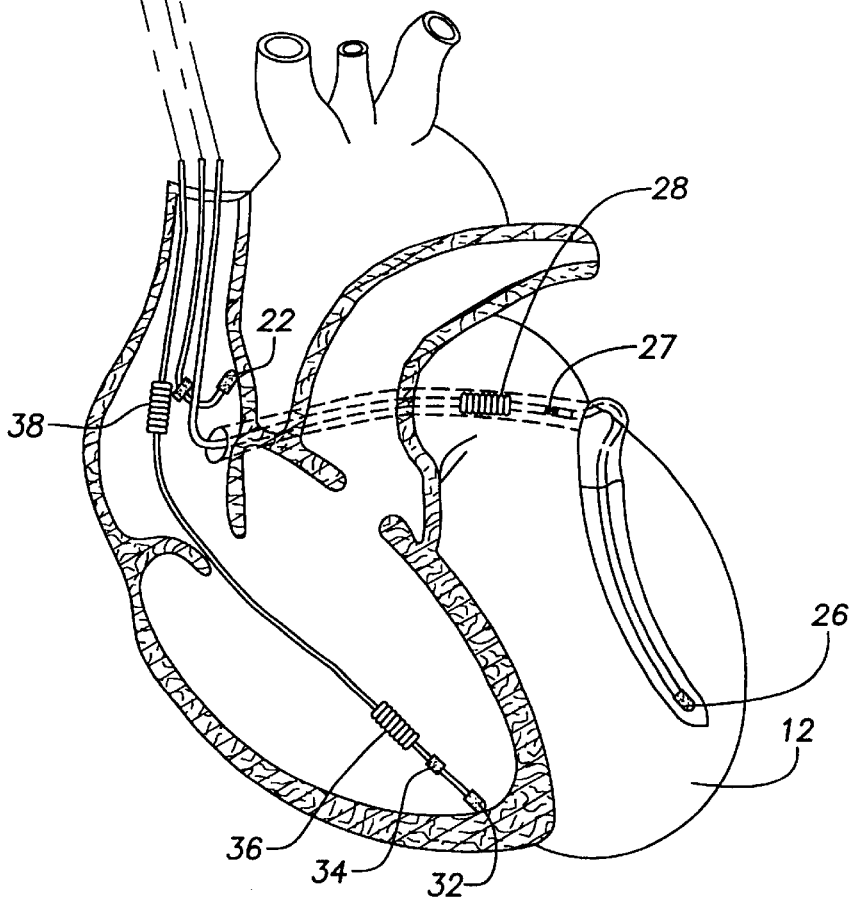
FIG. 1

METHOD AND APPARATUS FOR TIMING EVENTS WITHIN AN IMPLANTABLE MEDICAL DEVICE

FIELD OF THE INVENTION

The invention generally relates to implantable medical devices and in particular to methods and apparatus for timing events within implantable medical devices capable of performing concurrent multiple processes, tasks or functions.

BACKGROUND OF THE INVENTION

A wide range of implantable medical devices used for cardiac rhythm management are provided for surgical implantation into humans or animals. Examples of cardiac rhythm management devices are cardiac pacemakers and cardioverter/defibrillators (ICD). Other examples include devices for stimulating or sensing portions of the brain, spinal cord, muscles, bones, nerves, glands or other body organs or tissues. State of the art implantable medical devices are typically configured to perform a variety of tasks concurrently. For example, a pacemaker or ICD may analyze cardiac rhythm signals received from the heart to identify any arrhythmias to permit therapy to be applied. Concurrently, the pacemaker or ICD may monitor the battery or other power source of the device to verify that the power source is capable of providing the appropriate voltage and current for functions such as pacing or defibrillation. Likewise, the device may concurrently monitor the impedance of leads connected to the heart to verify that there are no faults in the leads. Some functions are unique to the particular implantable medical device. For example, an ICD contains capacitors for use in generating a defibrillation pulse. For proper operation, the capacitor needs to be reformed periodically every two to four months to prevent charge time degradation. Accordingly, the ICD periodically performs a capacitor reformation function. A wide variety of other tasks maybe performed as well by the implantable medical device. In many cases, the tasks are performed by a microprocessor of the device. In other cases, separate dedicated hardware components of the device are employed.

Many of the tasks performed by the implantable medical device require that certain periods of time be tracked to facilitate completion of the task. For example, to analyze cardiac rhythm signals, the corresponding function may require that each cardiac pulse, i.e. each individual or components of the QRS complex, be timed with respect to others. As such, a timer capable of measuring time lasting in the order of a few to hundredths of milliseconds is required. For other functions, such as monitoring the power source or the leads or for performing capacitor reformation, the time periods that need to be timed are on the order of minutes, hours, weeks, months, or years.

To time an event, a software component such as (but not limited to) a task, object, function, subroutine, in-line code, interrupt service routine, operating system call, mainline code, etc.) typically makes a request to a timer manager or operating system component. The request specifies that an interrupt be generated by a hardware timer incorporated within the device following the expiration of a predetermined amount of time (or that some other timer completion signal be generated). For timing short-term events, such as events spanning only a few milliseconds, a timer with eight or sixteen bits may be required. To time even longer events, such as events spanning hours, weeks, months, or years, a timer having sufficient memory bits (32, 64 or 128 bits) to register the long periods of time is required. Such timers are also commonly found in desktop computers, laptop commuters, cellular telephones and the like. To accommodate the possibility of several concurrent processes, several such timers are often employed, each providing high timing resolution and others having sufficient memory to accommodate long time duration.

However, within implantable medical devices it is critical that the size of the device and the amount of power consumed by the device be minimized. Power must be minimized to ensure that the power supply lasts for several years. The size of the device must be minimized to make it as light as possible to reduce discomfort to the patient after the device has been implanted. Unfortunately, with implantable medical devices implemented using timing devices as described above, neither device power nor device size is minimized. A set of hardware timers each counting time in parallel is an undesirable expenditure of power.

Size of the device is not effectively minimized because each timer requires a large number of memory registers to accommodate the potentially large timing periods. Hence, the physical size of an integrated circuit or other device used to implement the timer is not minimized. Moreover, with each timer configured to accommodate long timing periods, considerable current is consumed powering the many memory registers of the counter.

As noted, if multiple concurrent processes need to be timed, the implantable medical device is often configured to provide several timers each providing high timing resolution and having sufficient memory to accommodate long timing durations. Accordingly, power consumption and device size increases accordingly. Furthermore, to accommodate the multiple processes and the multiple timers, numerous timer requests need to be generated and tracked, resulting in an increase in the overall system complexity.

Thus, it would be desirable to provide an improved hardware timing system for use within an implantable medical device and it is to that end that aspects of the invention are primarily directed.

SUMMARY OF THE INVENTION

In accordance with the invention, a device is provided for timing hardware or software events for use in an implantable medical device capable of performing a plurality of concurrent processes using a hardware timer capable of timing events up to a pre-determined maximum period of time. Means are provided for receiving timer requests from the plurality of processes with each timer request specifying a time delay before a timer interrupt or other timer completion signal is required, wherein the time delay of each individual timer request is no greater than the maximum period of time. The device includes a timer request processing means for controlling the hardware timing means to issue interrupt signals or other timer completion signals based upon the time delays of the timer request requests. The timing request processing means determines, upon receipt of each new timer request, the next timer request that needs to be timed and the time remaining to issue the next interrupt or other timer completion signal and sequentially controlling the timing means to time each remaining period of time between successive timer requests.

In an exemplary embodiment of the invention, the device is either an implantable cardioverter defibrillator or a pacemaker. The hardware timing means is a downcount hardware timer having a resolution of about one millisecond. The timing request processing means employs a pseudo clock, which is an arbitrary record of elapsed time having an effective timing resolution of about one millisecond. Both the hardware timer and the timing request processing means employ counters storing two bytes of information, incremented by one bit after each timing interval. The maximum pre-determined period of time is about sixty-four seconds.

By employing the concept of the pseudo clock, the device may efficiently time a plurality of concurrent processes using only a single hardware timer. Hence, a separate timer is not required for each process and a substantial reduction in power and required circuit space is achieved. Also, the overall system complexity is reduced as compared to a system requiring coordination of multiple timers.

Other objects and advantages of the invention are provided as well. Method embodiments of the invention are also provided. Preferably, an implantable medical device configured in accordance with the invention implements and exploits both the first and second aspects of the invention by employing both short-term and long-term timers, each having an associated pseudo clock.

BRIEF DESCRIPTION OF THE DRAWINGS

Further features and advantages of the invention may be more readily understood by reference to the following description taken in conjunction with the accompanying drawings, in which:

FIG. 1 is a simplified diagram illustrating an implantable stimulation device in electrical communication with at least three leads implanted into a patient's heart for delivering multi-chamber stimulation and shock therapy;

DETAILED DESCRIPTION OF THE PREFERRED EMBODIMENTS

Figure 2:
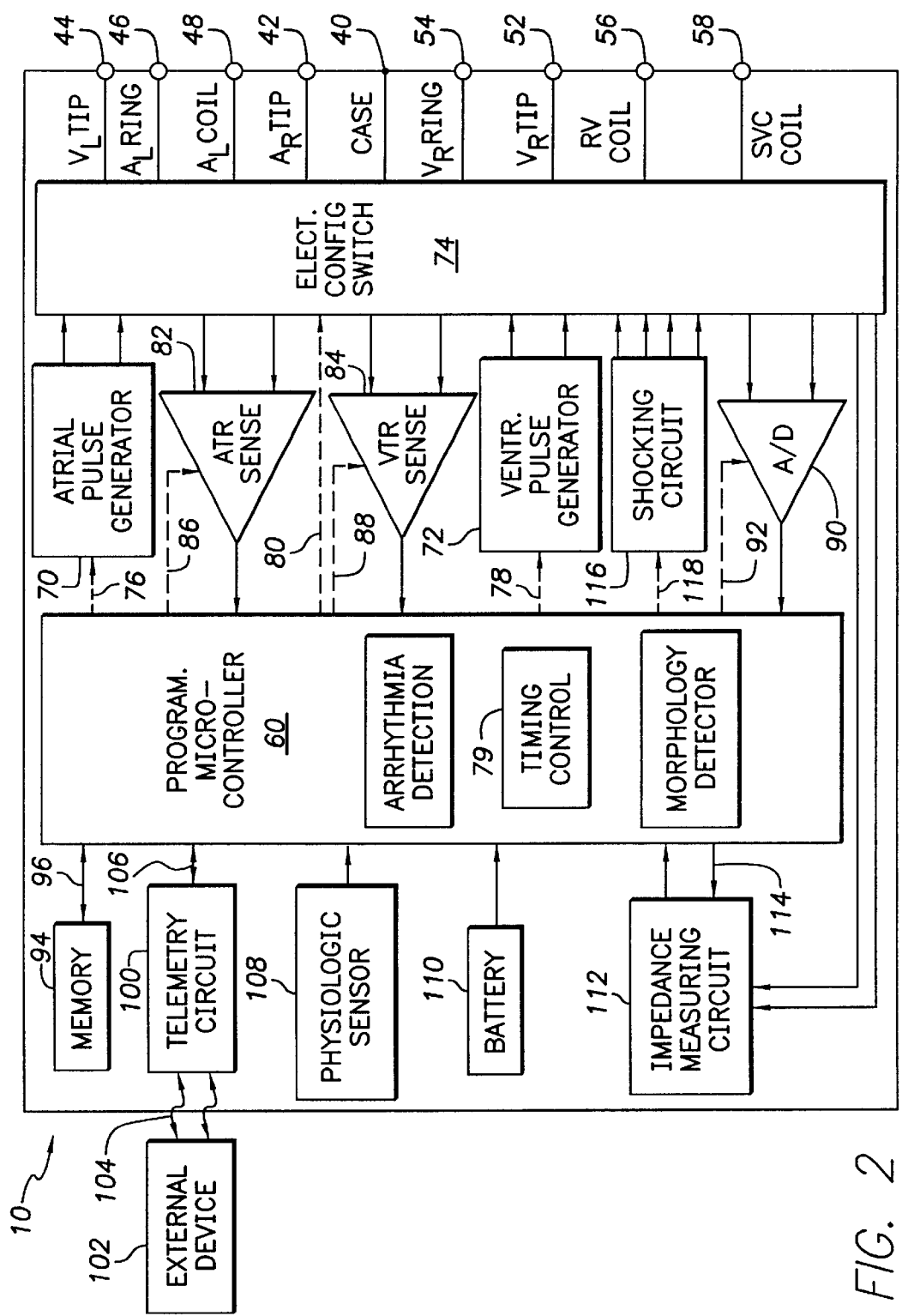
FIG. 2 is a functional block diagram of a multi-chamber implantable stimulation device illustrating the basic elements of a stimulation device, which can provide cardioversion, defibrillation and pacing stimulation in four chambers of the heart.

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, "A Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et al.), the state-machine of U.S. Pat. Nos. 4,712,555 (Sholder) and 4,944,298 (Sholder). For a more detailed description of the various timing intervals used within the stimulation device and their inter-relationship, see U.S. Pat. 4,788,980 (Mann et al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-Waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (AID) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110, which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical to the invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5 –10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

As noted, timing control unit 79 times various events (e.g., pacing rate, atrio-ventricular (AV) delay, atrial interconduction (A—A) delay, or ventricular interconduction (V—V) delay, refractory periods, PVARP intervals, noise detection windows, evoked response windows, alert intervals, marker channel timing, etc. Typically, the events are timed on behalf of software processes running in the controller 60 or on behalf of other hardware components of the overall device, such as the impedance measuring circuit. Herein below, hardware or software components issuing timer request are simply referred to as functional units. Once an event has been timed, the timer control unit issues an interrupt or other timer completion signal. Some of the timer requests require interrupts or other timer completion signals to be generated after only a few milliseconds, others requiring interrupts after several minutes, hours, weeks, months or years. As will be described in more detail below, timer control unit 79, in combination with other elements of controller 60, is configured to efficiently and expediently process the timer requests while consuming relatively little power from battery 110 and without requiring any substantial hardware resources.

One technique by which the timing control unit processes both short-term and long-term timer request requests will now be described with reference to FIG. 3. Timing control unit 79 includes a high resolution/short duration hardware timer 116 and a separate low resolution/long duration hardware timer 118. High resolution timer 116 is configured to time events up to a maximum of 65 seconds with a resolution of one millisecond. To this end, the high resolution timer employs a two byte binary counter 120 updated, when in use, once every millisecond. Low resolution timer 118 is configured to time events up to a period of 240 years at a resolution of two seconds. To this end, the low resolution timer receives a clock signal or other interrupt source having a period of two seconds. Timer system 112 additionally includes a timer manager 124 that receives timer request requests from functional units of the overall implanted device (FIG. 2) and selects, based upon the duration of the timer request request, the appropriate timer for use in timing the request. All timer request requests specifying a time period of less than two seconds are routed to the high resolution timer 116. All timer request requests specifying a time period over 65 seconds are routed to the low resolution timer. For timer request requests specifying time periods from two seconds to 65 seconds, the timer manager determines the degree of resolution required and selects the timer accordingly. For example, if a timer request is issued by a functional unit that does not require high resolution, then the timer request is forwarded to the low resolution timer, even though it could alternatively be timed using the high resolution timer. In contrast, if a timer request is received specifying a time period of ten seconds from a functional unit requiring a high degree of timing resolution, then the timing manager times the timer request using the high resolution timer to thereby insure that the requisite degree of resolution is achieved.

Thus, the timer manager selects the appropriate timer for timing particular timer requests based upon the duration specified by the timer request, and perhaps by the resolution required for the timing operation. To this end, the timer manager may include a table listing all timer requests that can be requested, and specifying the appropriate timer to be used in each case. In a specific implementation, the short-term timer is employed for timing timer requests used in connection with telemetry, bradycardia monitoring, non-invasive programmer stimulation, internal electrocardiogram detection and storage, and morphology monitoring. The long-term timer is selected for timing timer requests used in connection with bradycardia monitoring, data measurement and recording, and diagnostics. Note that the bradycardia-monitoring unit uses both the long-term and short-term timers.

Figure 3:
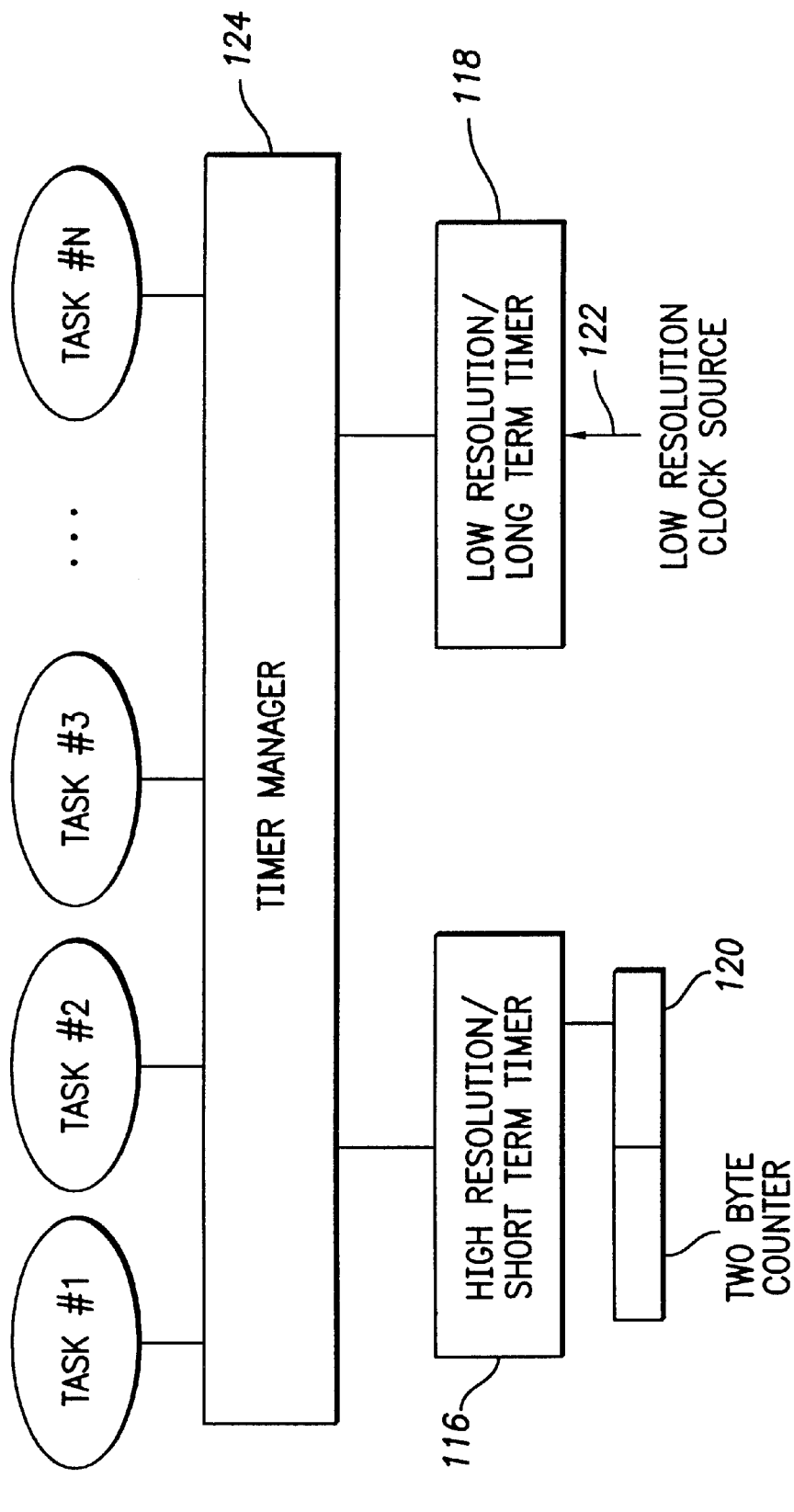
FIG. 3 is a block diagram illustrating a timer system employed by the pacemaker of FIG. 1 wherein a short term/high resolution timer and a separate long term/low resolution timer are employed.

By employing two separate timers, one optimized for high resolution/short duration timing and the other optimized for low resolution/long duration timing, the timer system of FIG. 3 saves power and circuit resources as compared to timer systems employing only a single timer capable of high resolution timing over a period of several years. Hence, a smaller amount of circuit space is required and less power is required for refreshing the storage registers. Also, the high resolution/short duration timer of FIG. 3 operates only when required. Accordingly, over the lifetime of the pacemaker, the high resolution timer may be operative only during a fraction of the total lifetime. Hence, significant power savings are achieved over a pacemaker employing a single high resolution/long duration timer which must consume power to increment the counter every millisecond merely to time events wherein interrupts are not required for days, months or years.

Thus, FIG. 3 illustrates a timer system employing separate high resolution and low resolution timers. The system is therefore easily capable of concurrently timing one short-term task and one long-term task using the separate timers. If the pacemaker requires that two or more short-term tasks be timed concurrently or that two or more long-term tasks be timed concurrently, then the pacemaker may be configured with additional high resolution timers and additional low resolution timers. In the alternative, though, the timer manager is preferably configured to utilize only a single high resolution timer and only a single low resolution timer to time multiple concurrent processes. To this end, the timer manager operates in conjunction with a pseudo clock to be described below.

Figure 4:
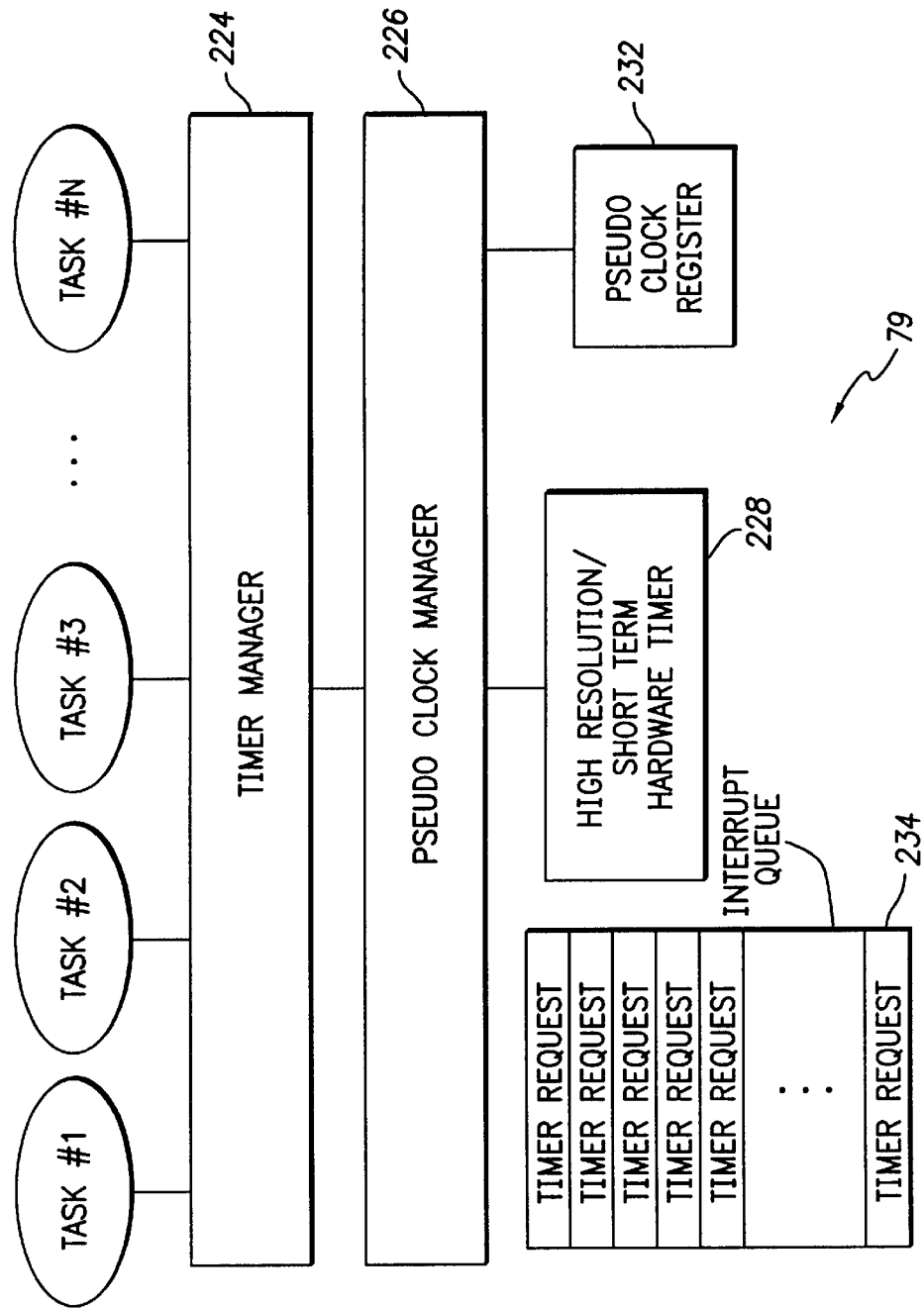
FIG. 4 is a block diagram illustrating an alternative timer system for the pacemaker of FIG. 1 wherein the concept of a pseudo clock is exploited.

FIG. 4 illustrates, at a high level, a system for processing multiple timer requests generated by concurrent processes using a pseudo clock. A timer manager 224 receives timer requests from any of a variety of individual tasks performed by the functional units (FIG. 2) or other requesting process. The timer manager routes the timer requests to a pseudo clock manager 226 which times each of the timer requests using a single hardware timer 228, which may be, for example, a high resolution/short duration timer, a low resolution/long duration timer, a low resolution clock signal. The pseudo clock itself is an artificial time value stored within a pseudo clock register 232, incremented in synchronization with the hardware timer. The pseudo clock manager also employs a timer request queue register 234 which stores an identification of each pending timer request along with a pseudo clock value representative of a time when the interrupt or other timer completion signal is to be issued. The operation of the pseudo clock will be described in greater detail below.

Figure 5:
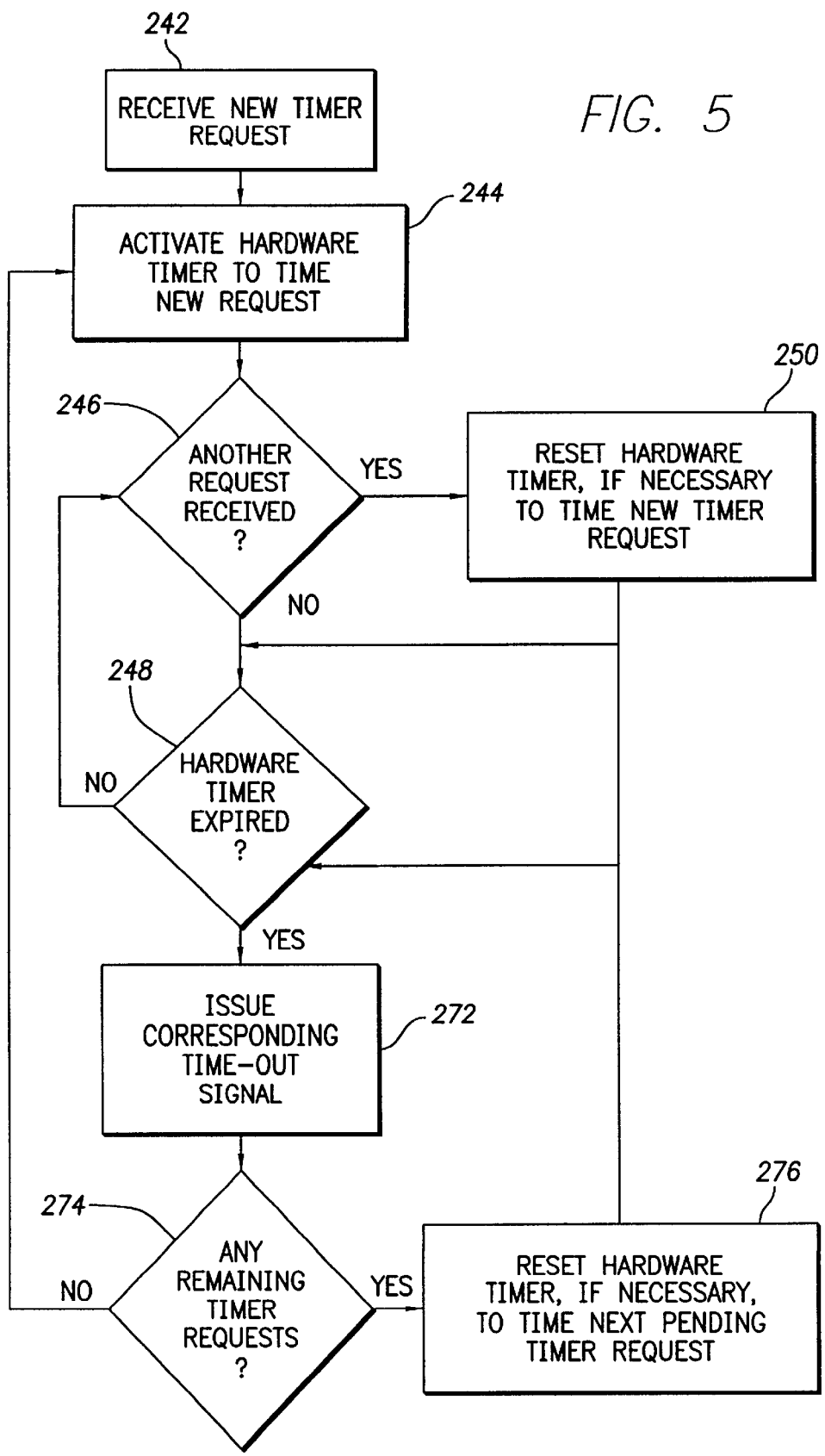
FIG. 5 is a flow chart illustrating steps performed by the timer system of FIG. 4.

FIG. 5 is a flow chart illustrating, at a high level, a method for processing multiple timer requests for multiple concurrent processes using a single hardware timer. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Initially, at step 240, the pseudo clock manager receives a timer request. If one is received, hardware timer 228 (FIG. 4) at step 244 is activated to time the timer request, i.e., the hardware timer is set to a value corresponding to the time delay value specified by the timer request. Once the hardware timer is activated, steps 246 and 248 are executed in a loop until either another timer request is received or until the hardware timer expires. Assuming a second timer request is received, then the hardware timer is reset, if needed, at step 250 to account for the new timer request.

Figure 6:
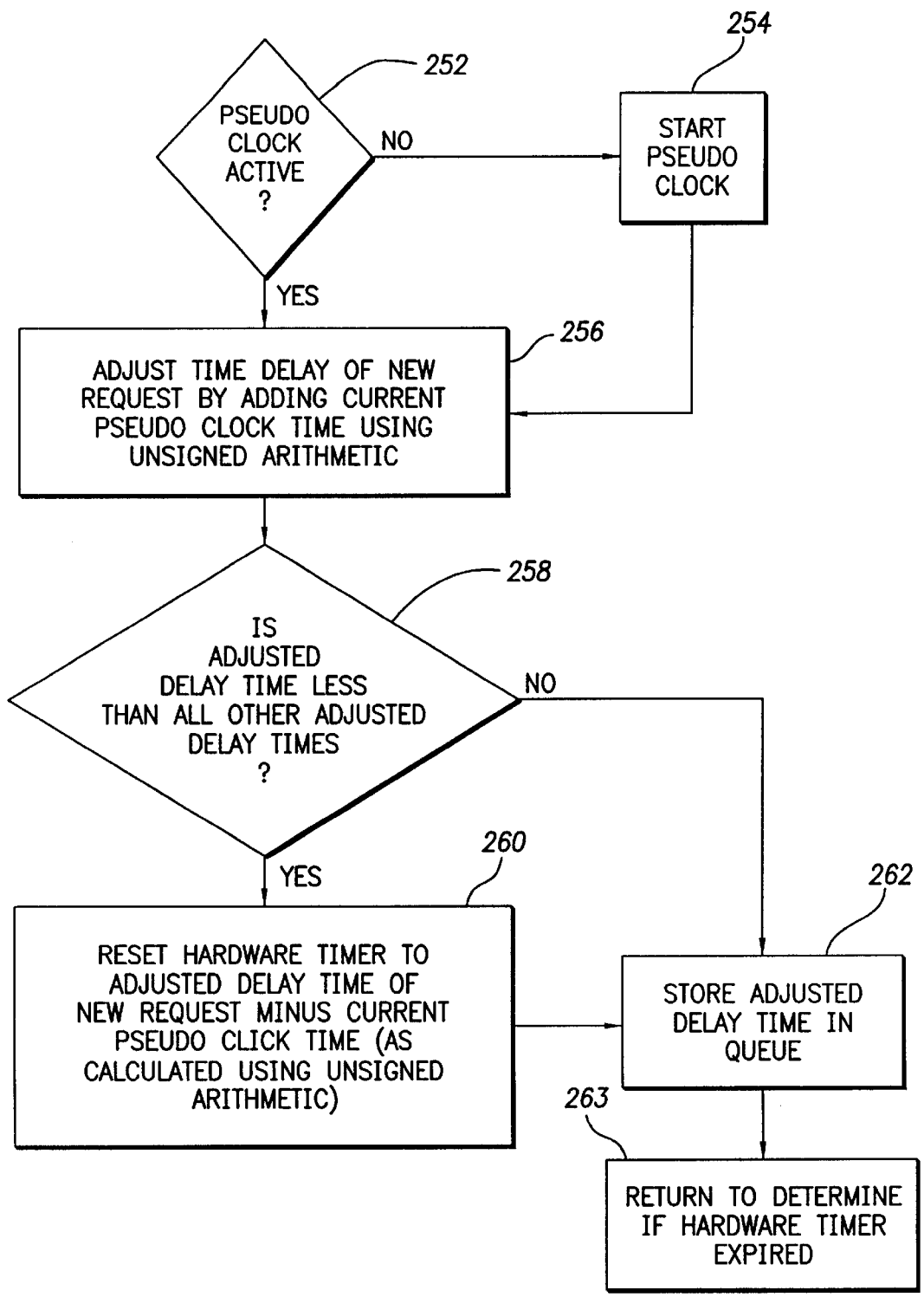
FIG. 6 is a flow chart illustrating sub-steps performed by the timer system of FIG. 4 for resetting the single hardware timer, if needed, upon receipt of a new software timer request.
Figure 7:
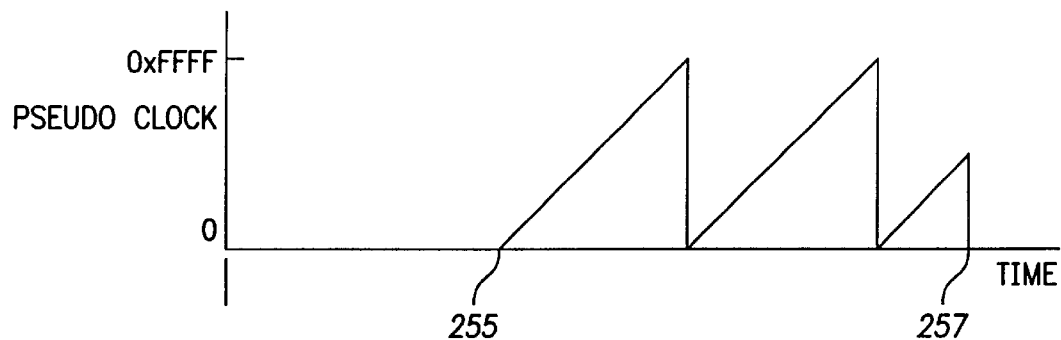
FIG. 7 is a graph illustrating the pseudo clock employed by the timer system of FIG. 4.

FIG. 6 illustrates, at a high level, one exemplary technique for resetting the hardware timer during step 250 by exploiting the concept of a pseudo clock. At step 252 of FIG. 6 the clock manager determines whether the pseudo clock is already activated and, if not, then the pseudo clock is activated at step 254. FIG. 7 graphically illustrates the pseudo clock. As can be seen, the pseudo clock is a hexadecimal clock value which increases linearly from zero beginning as soon as at least two timer requests are pending, which is identified in FIG. 7 by reference numeral 255. To this end, the pseudo clock manager tracks a value "number active TQE" representative of the number of pending timer requests. In the exemplary embodiment, the pseudo clock has sufficient memory to register up to 64 seconds with each binary count of the pseudo clock translating to 976.5625 microseconds. When the pseudo clock reaches 64 seconds, or a hexadecimal value of 0XFFFF, the pseudo clock overflows and starts counting again from 0X00, thus yielding the saw-toothed pattern shown in FIG. 7. Also, the pseudo clock is terminated once the number of pending timer requests is reduced to only zero or one, which is identified in FIG. 7 by reference numeral 257.

Referring again to FIG. 6, the time delay value specified by the newly received timer request is reset, at step 256, to be equal to the time specified plus the current value of the pseudo clock. Assuming that the pseudo clock has just been activated, then step 256 merely results in the number zero being added to the specified time. However, if the pseudo clock is already active as a result of a previous timer request, then the time delay value for the new timer request is adjusted by the addition of the current value of the pseudo clock. Note that the arithmetic operation of step 256 is performed using unsigned arithmetic such that, if the sum of the time delay value and the current value of the pseudo clock exceeds 64 seconds, then the resulting value will nevertheless be within the range of zero to 64 seconds. In this manner, the timer request delay time for the new timer request is always set to a pseudo clock time within the range of zero to 64 seconds.

At step 258, the clock manager then determines whether the newly received timer request has an adjusted value less than the adjusted values of all other pending timer requests. If so, then, at step 260 the hardware timer is reset to the adjusted time value minus the current pseudo clock value such that the hardware timer can time the newly received timer request. Thereafter, at step 262, the adjusted time value of the newly received timer request is stored along with all other pending timer requests in the timer request queue 234 (FIG. 4). If, on the other hand, the adjusted time value of is not less than the adjusted values of all other timer requests, step 260 is not performed and execution proceeds directly to step 262. In either case, at step 263, execution returns to step 248 of FIG. 5 to determine if the hardware timer has expired.

In this manner, the hardware timer is reset, if necessary, to time the newly received timer request. Otherwise, the hardware timer is not reset and instead continues to time the previously received timer request having the lowest adjusted time value. Hence, the hardware timer always is set to time the timer request that needs to be issued next.

Figure 8:
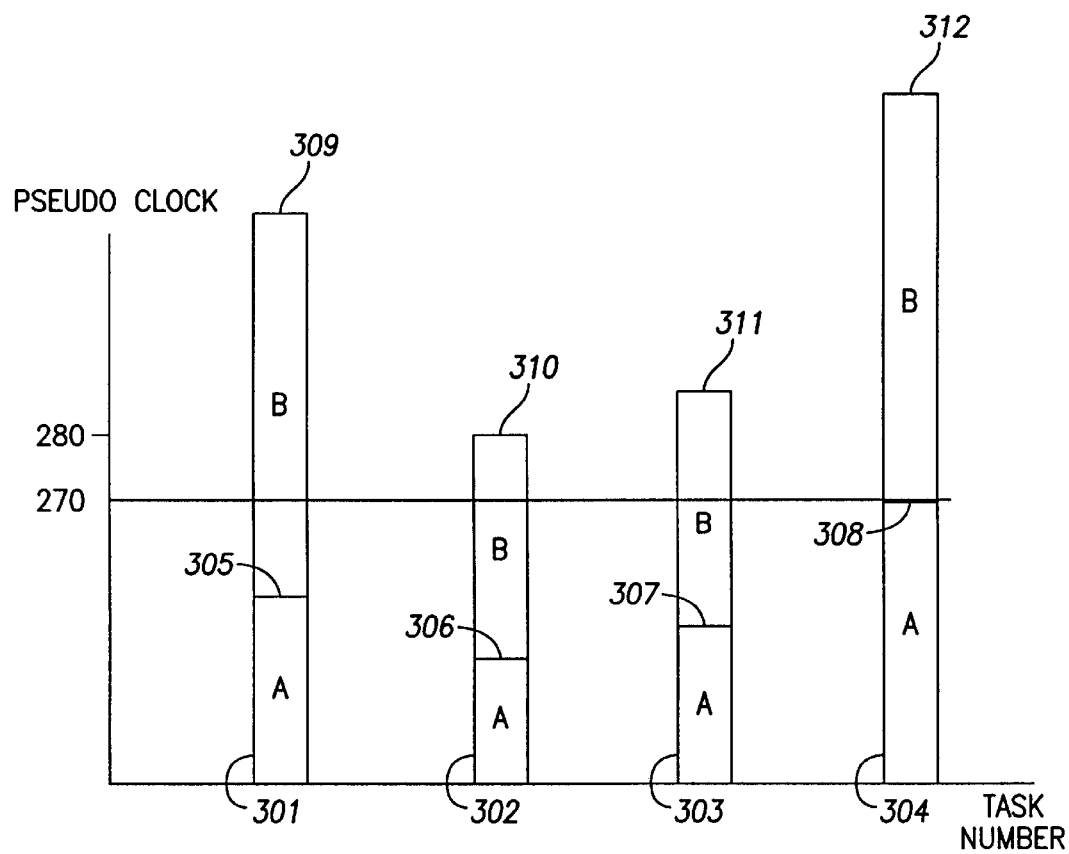
FIG. 8 is a block diagram illustrating a relationship between the pseudo clock, the hardware timer, and four concurrent software process timer request requests.

The relationship between the pseudo clock and the individual timer requests is graphically illustrated in FIG. 8. Briefly, FIG. 8 illustrates four timer requests 301–304. For each timer request, FIG. 8 also illustrates the pseudo clock time value when the timer request was first received 305–309 and the pseudo clock value when the corresponding timer request needs to be issued 310–314. As can be seen, timer request 302 was received first and must be issued first. Timer request 304 was received last and must be issued last. However, in general, there may be no correlation between when a timer request is received and when it must be issued. The first request received may need to be issued last and that last request received may need to be issued first. The actual time delay value for each timer request represents the time between when a timer request was received and when it must be issued. This time delay value is identified in FIG. 8 as "B". This is the value received as part of the timer request.

The example of FIG. 8 will now briefly be summarized with reference to the steps of FIG. 6. At pseudo clock time 270, timer request 304 is received. At that time, timer requests 301–303 are already pending. Accordingly, the pseudo clock is already operational. At step 270, the time delay value B specified by timer request 304 is added to the current pseudo clock time to yield adjusted time 312. This adjusted time is compared with adjusted times 309–311 to determine if it is less than the others and, since it is not, the hardware timer is not reset. In contrast, if timer request 302 were not received until time 270, then the hardware timer would be reset because the adjusted time value 310 for that timer request would be less than the adjusted time values for the other timer requests. Also note that the addition of the current pseudo clock time with the time delay value B for each timer request is performed using unsigned arithmetic. Accordingly, adjusted value 312 may actually be numerically less than the current pseudo clock time and numerically less than the adjusted times for the other pending timer requests. Hence, at step 258 of FIG. 5, when determining whether the adjusted time for the newly received timer request is less than the adjusted times for the other timer requests, the clock manager first identifies all timer requests having adjusted values exceeding the current pseudo clock value and then identifies the lowest adjusted value of that group. If none of the adjusted values exceeds the current pseudo clock value, then the clock manager identifies the timer request having the lowest absolute adjusted value. In any case, following the sub-steps of FIG. 6, hardware timer 228 (FIG. 4) is reset, if needed, to time the timer request that needs to be issued next.

Following completion of step 250 of FIG. 5, execution returns to the loop defined by steps 246 and 248 until either another new timer request is received or until the hardware timer expires. As can be appreciated, numerous timer requests may be received before the timer expires, each causing the timer to be reset to a different time value. Ultimately, the timer expires indicating that at least one of the pending timer requests needs to be issued. If so, then the timer request is issued at step 272 by the clock manager. In this regard, the clock manager examines the timer request queue of register 234 (FIG. 4) to identify the particular timer request that needs to be issued, then issues that interrupt or other timer completion signal to the process requesting the timer request. This may be achieved by comparing the current pseudo clock value at step 272 with the adjusted pseudo clock values listed along with each timer request in the queue register to identify a match. In the alternative, the timer request queue can be configured as a first in/first out queue with the entries in the queue being re-sequenced, as needed, whenever a new timer request is received that necessitates a reset of the hardware timer.

Following step 272 of FIG. 5, the clock manager then determines at step 274 whether there are any other currently pending timer requests. If not, execution simply returns to step 240 for receiving a subsequent timer request. If, however, there is at least one currently-pending timer request then execution immediately proceeds to step 276 wherein the hardware timer is reset to time whichever pending timer request needs to be issued next.

Figure 9:
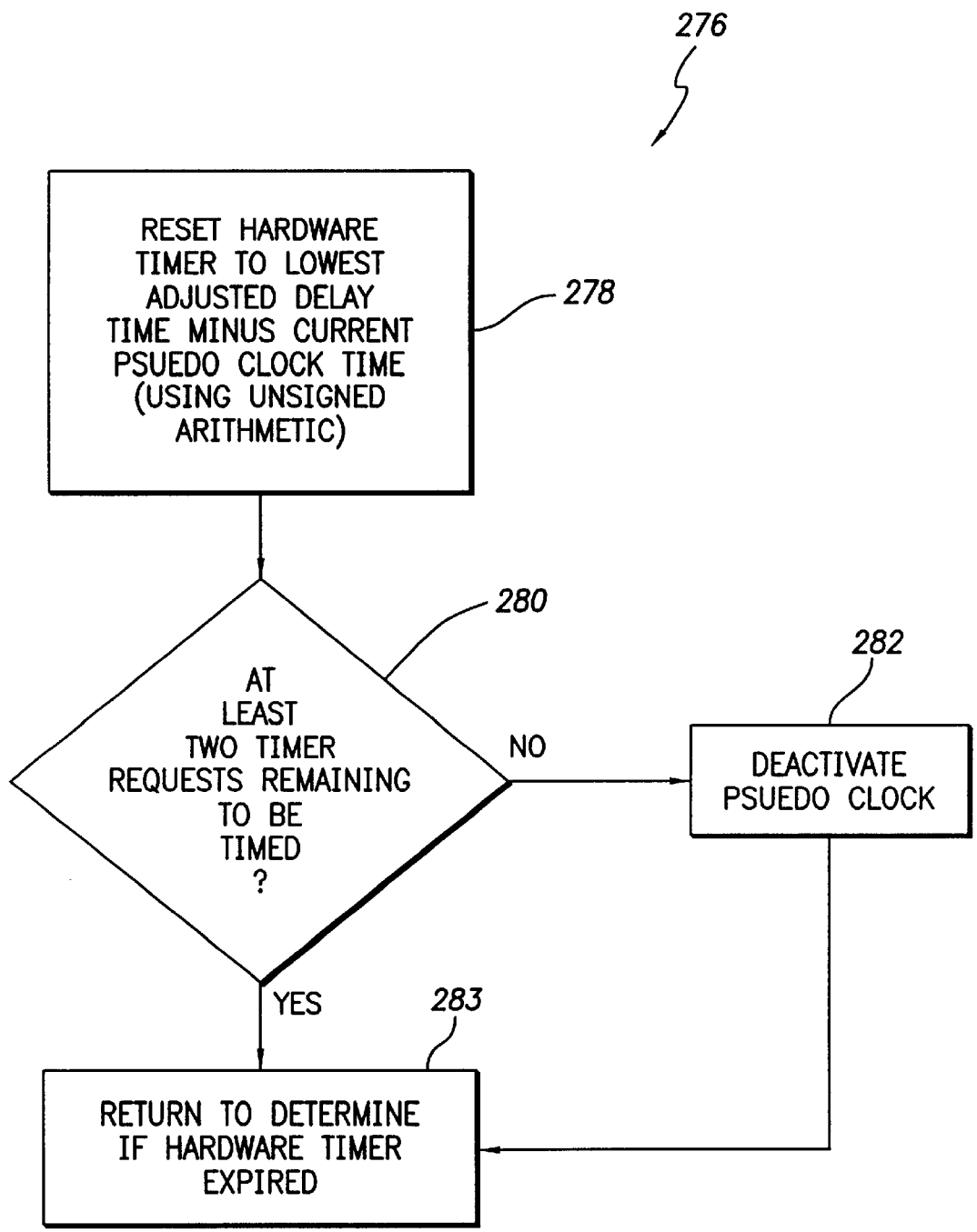
FIG. 9 is a flow chart illustrating sub-steps of the method of FIG. 5 employed to reset the hardware timer following issuance of each interrupt or other timer completion signal.

FIG. 9 illustrates, at a high level, one exemplary technique for resetting the hardware timer to time a next pending timer request during step 250 by exploiting the concept of a pseudo clock. At step 278 the clock manager identifies the timer request that needs to be issued next by examining the adjusted time delay values for each pending timer request stored within the timer request queue 234 (FIG. 4). As before, this operation is performed with unsigned arithmetic and care should be taken to account for the possibility that the adjusted time value for the interrupt or other timer completion signal that needs to be issued next may have a lower pseudo clock value than the current value of the pseudo clock. In the example of FIG. 8, once timer request 302 is issued at time 280, the clock manager will determine that timer request 303 needs to be issued next and the hardware timer is reset to time the remaining time delay value between the adjusted time of request 303 and the current pseudo clock time 280. Then, at step 282 of FIG. 9, the clock manager determines the total number of pending timer requests. If there are fewer than two pending timer requests, then the pseudo clock is disabled at step 282 and execution returns via step 283 to step 248 of FIG. 5 to determine if the hardware timer has expired. If there are at least two pending timer requests, then the pseudo clock is not disabled. Instead, execution proceeds immediately to step 248 of FIG. 5. Thus, in either case, execution returns to the loop defined by steps 246 and 248 of FIG. 5 where execution continues in a loop until either another timer request is received or until the hardware timer expires again.

Ultimately, all pending timer requests are processed and execution returns to step 240 to await a new timer request.

Thus, the pseudo clock manager, in combination with a single hardware timer, the queue register and the pseudo clock operates to process numerous pending timer requests from numerous concurrent processes using only a single hardware timer. The total number of timer requests that can be accommodated depends only upon the size of the timer request queue and upon any limitations in the software of the pseudo clock manager. If the timer request queue has storage for 16 entries, then a total of 16 pending timer requests can be accommodated. Thus, a substantial reduction in circuit space is achieved over systems that would require a separate timer for each separate pending timer request. Corresponding power savings are achieved as well. Also, by performing all arithmetic operations in connection with the pseudo clock using unsigned arithmetic, the pseudo clock itself need not require any more storage registers than the hardware timer. Also, the ability to exploit unsigned arithmetic allows less complex hardware and software to be employed in performing the arithmetic calculations. Also, the use of the pseudo clock permits both the hardware timer and the pseudo clock memory register to be relatively small. In the example thus far described, the hardware timer and pseudo clock register employ storage registers for timing only 64 seconds worth of time. Yet, when used in combination, the hardware timer and the pseudo clock permit a sequence of timer requests to be processed over a much longer period of time. The only limitation is that each individual timer request be for a time period of less than or equal to 64 seconds. A sequence of timer requests can collectively combine to substantially more than 64 seconds. Indeed, so long as new timer requests are received such that there are at least two pending timer requests at all times, the hardware timer and pseudo clock operate indefinitely.

Although described with reference to an example wherein the hardware timer provides counters for timing up to 64 seconds at a resolution of one millisecond, in other implementations other hardware timers may be employed. In the preferred embodiment, the 64-second timer is employed because most timer requests requiring high resolution timing specify a time delay of no more than 64 seconds. For timer requests requiring a longer time period, the aforementioned long-term/low resolution timer is employed. In alternative implementations wherein all timer requests requiring high resolution timing specify a time delay value of less than ten seconds, then a hardware timer capable of timing only ten seconds is preferably employed. In still other embodiments wherein some timer requests requiring high resolution timing specify a time delay value of greater than 64 seconds, a hardware timer capable of timing longer periods of time is preferably employed. As can be appreciated, the size of the hardware timer can therefore be optimized in accordance with the timer requests expected to be received.

In the embodiments thus far described, the pseudo clock is exploited only in connection with the high resolution timer. In other implementations, including the detailed implementation to be described below, the pseudo clock is also exploited in connection with the low resolution timer.

What has been described are systems and methods for timing events within pacemaker as other implantable medical device. The various functional components of the exemplary system may be implemented using any appropriate technology including, for example, microprocessors running software programs or application specific integrated circuits (ASICs) executing hard-wired logic operations. Although described with respect to a pacemaker, aspects of the invention are applicable to other implantable medical devices such as ICDs. The exemplary embodiments of the invention described herein are merely illustrative of the invention and should not be construed as limiting the scope of the invention.

What is claimed is:

1. In an implantable cardiac rhythm management device having a processing components capable of performing a plurality of concurrent tasks, a timing device for timing events in such rhythm management device, the timing device comprising:

a hardware timer operative to time events up to a pre-determined maximum period of time;

a timer manager operative to receive timer requests from the plurality of processes with each timer request specifying a time delay to be timed, wherein the time delay of each individual timer request is no greater than the maximum period of time; and a timer manager operative to control the hardware timer to issue timer completion signals based upon the time delays of the timer requests, the timer manager determining, upon receipt of each new timer request, the next timer completion signal that needs to be issued and the time remaining to issue next timer completion signal and sequentially controlling the hardware timer to time each remaining period of time between successive timer requests, the determination being made with comparison to a pseudo clock value such that only a single timer is required.

2. The timing device of the implantable cardiac rhythm management device of claim 1 wherein the processing components perform processes including telemetry, bradycardia monitoring, data measurement and recording, non-invasive programmer stimulation, high voltage control, diagnostics, internal electrocardiogram detection and storage and morphology monitoring.

3. The timing device of the implantable cardiac rhythm management device of claim 1 wherein the implantable cardiac rhythm management device is either a pacemaker or a cardioverter/defibrillator.

4. In an implantable cardiac rhythm management device having a processing components capable of performing a plurality of concurrent tasks, a timing device for timing events in such rhythm management device, the timing device comprising:

a timing means for timing events, the timing means capable of timing events only up to a pre-determined maximum period of time;

means for receiving timer requests from the plurality of processes with each timer request specifying a time delay to be timed, wherein the time delay of each individual timer request is no greater than the maximum period of time; and timing means for controlling the timing means to issue timer completion signals based upon the time delays of the timer requests, the timing means determining, upon receipt of each new timer request, the next timer completion signal that needs to be issued and the time remaining to issue the next timer completion signal and sequentially controlling the timing means to time each remaining period of time between successive timer requests, the determination being made with comparison to a pseudo clock value such that only a single timer is required.

5. The timing device of the implantable cardiac rhythm management device of claim 4 wherein the processing components perform processes including telemetry, bradycardia monitoring, data measurement and recording, non-invasive programmer stimulation, high voltage control, diagnostics, internal electrocardiogram detection and storage and morphology monitoring.

6. The timing device of the implantable cardiac rhythm management device of claim 4 wherein the implantable cardiac rhythm management device is either a pacemaker or a cardioverter/defibrillator.

7. The timing device of the implantable cardiac rhythm management device of claim 4 wherein the timing means includes:

determination means for determining a current amount of time remaining before the timing means issues a timer completion signal based upon a previously requested timer request; and comparison means for determining whether the time delay for a newly requested timer request is less than the time remaining on the timing means and, if so, for resetting the timing means to issue a timer completion signal following the time delay of the newly requested timer request and, if not, for waiting until the timing means issues a timer completion for a first timer completion signal that needs to be issued then for resetting the timing means to issue a second timer completion signal following a time remaining for a next timer completion signal that needs to be issued.

8. In an implantable cardiac rhythm management device having a processing components capable of performing a plurality of concurrent tasks, a method for timing events in such rhythm management device using a hardware timer capable of timing events only up to a pre-determined maximum period of time and a counter, the method comprising the steps of:

a) receiving a first timer request requesting that a first duration of time be timed, the first duration of time being no greater than the maximum pre-determined time;

b) activating the timer to time the first duration of time;

c) receiving a second timer request requesting that a second duration of time be timed, the second duration of time being no greater than the maximum pre-determined time;

d) controlling the counter to operate as pseudo clock beginning at the point in time the second timer request is received;

e) receiving additional timer requests, each specifying a duration of time no greater than the maximum pre-determined time and, for each additional timer request, adding a current value of the pseudo clock to the corresponding specified duration of time to yield an adjusted duration of time;

f) as each additional timer request is received, determining the current pseudo clock time, determining which pending timer request needs to be timed next by comparing the adjusted times of the timer requests with the current pseudo clock time, then resetting the hardware timer to time the remaining time for that timer request;

g) issuing a timer completion signal when the hardware timer expires; and h) repeating steps e), f) and g) until all pending timer requests have been processed.

9. In an implantable cardiac rhythm management device having a processing components capable of performing a plurality of concurrent tasks, a method for timing events in such rhythm management device using a timer capable of timing events only up to a pre-determined maximum period of time and a counter, the method of timing comprising the steps of:

receiving a plurality of concurrent timer requests from the plurality of processes with each timer request specifying a time delay to be timed, wherein the time delay of each individual timer request is no greater than the maximum period of time;

upon receiving a first of the plurality of concurrent timer requests, activating the timer to time the respective time delay;

upon receiving a second of the plurality of concurrent timer requests, activating the counter to operate as a pseudo clock;

determining, upon receipt of each additional timer request, the timer request that needs to be completed next and the period of time remaining, the determination being made with comparison to a current value of the pseudo clock; and adjusting the timer to time the period of time remaining for the timer request that needs to be completed next and controlling the timer to issue a timer completion signal upon expiration of the timer.

10. The method of timing of claim 9 further comprising the steps of:

sequentially controlling the timer to time each remaining period of time between successive timer requests, and controlling the timer to issue additional timer completion signals upon each sequential expiration of the timer.

11. The method of timing of claim 9 wherein the step of adjusting the timer includes steps of:

determining a current amount of time remaining before the timer issues a timer completion signal based upon a previously requested timer request; and determining whether the time delay for a newly requested timer request is less than the time remaining on the timer and, if so, resetting the timing means to issue a timer completion signal following the time delay of the newly requested timer request and if not, waiting until the timer issues a first timer completion signal that needs to be issued then resetting the timer to issue a second timer completion signal following a time remaining for a next timer completion signal that needs to be issued.

12. The method for timing events of claim 9 wherein the processing components of the implantable cardiac rhythm management device perform one or more of the steps of telemetry, bradycardia monitoring, data measurement and recording, non-invasive programmer stimulation, high voltage control, diagnostics, internal electrocardiogram detection and storage and morphology monitoring.

* * * * *